US00PP33516P2

(12) United States Plant Patent
Scheiber et al.

(10) Patent No.: US PP33,516 P2
(45) Date of Patent: Sep. 28, 2021

(54) *ABELIA* PLANT NAMED 'ABESRPRAS'

(50) Latin Name: ***Abelia* hybrid**
Varietal Denomination: Abesrpras

(71) Applicant: THE CONARD PYLE COMPANY, West Grove, PA (US)

(72) Inventors: Sloane Scheiber, Cochranville, PA (US); Jessica Janes, Cochranville, PA (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 17/137,736

(22) Filed: Dec. 30, 2020

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP18,834 P2 5/2008 Robacker et al.

OTHER PUBLICATIONS

"Shrubs Vines Trees Evergreens Edibles" 2021 Star® Roses and Plants Catalog, published on Feb. 23, 2020, pp. 2, 9, 31, and 86.

*Primary Examiner* — Annette H Para
(74) *Attorney, Agent, or Firm* — Panitch Schwarze Belisario & Nadel LLP; Stephany G. Small; Travis W. Bliss

(57) ABSTRACT

A new and distinct variety of *Abelia* plant, referred to by its cultivar name, 'Abserpras', is disclosed. The new variety forms attractive light pink colored flowers with dark pink colored sepals. Attractive, medium green colored foliage is formed. The growth habit is compact and mounded. The new variety is well suited for providing attractive ornamentation in the landscape.

2 Drawing Sheets

Figure 1:
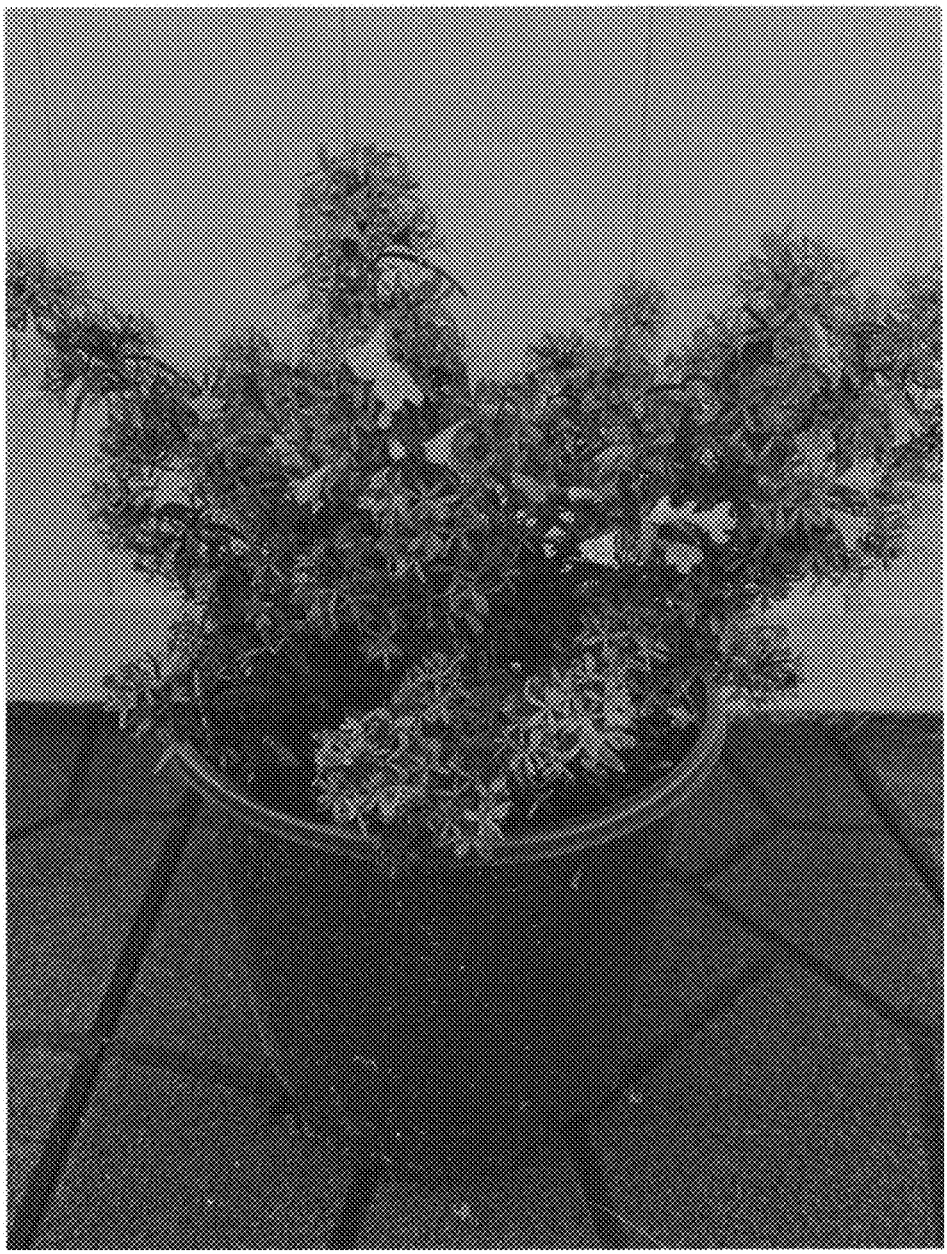

Botanical/commercial classification:
Latin name: *Abelia* hybrid.
Varietal denomination: 'Abesrpras'.

SUMMARY OF THE INVENTION

The new variety of *Abelia* hybrid plant originated in a controlled breeding program in Cochranville, Pa. during July, 2013. The objective of the breeding program was the development of *Abelia* cultivars with compact habits and a range of foliage colors. The new cultivar was created by open-pollination. The female parent (i.e., the seed parent) was an unnamed breeder seedling (non-patented). The male parent (i.e., the pollen parent) was unknown.

The parentage of the new variety can be summarized as follows:

unnamed breeder seedling x unknown

The new cultivar was discovered and selected as a single flowering plant from the progeny resulting from the above pollination during August, 2016 in a controlled environment in Cochranville, Pa. Selective study resulted in the identification of a single plant of the new variety.

It was found that the new variety of *Abelia* plant of the present invention:

(a) forms light-pink colored flowers with dark pink colored sepals,
(b) displays medium green colored foliage, and
(c) exhibits a moderately vigorous, compact and mounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed breeder seedling female parent variety (i.e., the seed parent) forms dark green colored foliage and provides an upright to rounded growth habit, whereas the new variety forms medium green colored foliage and provides compact and mounded growth habit. Moreover, the new variety can also be distinguished from other similar varieties that are commercially available. For instance, the new variety of the present invention can readily be distinguished from the 'Raspberry Profusion' variety (U.S. Plant Pat. No. 18,834), as the new cultivar displays a more compact and more rounded growth habit than the 'Raspberry Profusion' variety and the new cultivar plants are better branched, which require less trims compared to plants of the 'Raspberry Profusion'.

The new variety has been found to undergo asexual reproduction by a number of routes, including terminal stem cuttings. Asexual propagation by terminal stem cuttings in Cochranville, Pa. since September 2016 has shown that the characteristics of the new variety are stable and are strictly transmissible by such asexual propagation from one generation to another. Accordingly, the new variety undergoes asexual propagation in a true-to-type manner.

The new variety has been named 'Abesrpras'.

The new variety was first offered for sale in the "SHRUBS VINES TREES EVERGREENS EDIBLES" 2021 *Star® Roses and Plants Catalog*, which was published on Feb. 23, 2020 by a joint inventor or by another who obtained the new variety directly or indirectly from a joint inventor.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Abesrpras' variety. The plants were grown in one-gallon pots for approximately five months outside at Cochranville, Pa. Plants were pinched once after transplant.

FIG. 1—illustrates a specimen of the plant displaying the overall growth and flowering habit—side view.

Figure 2:
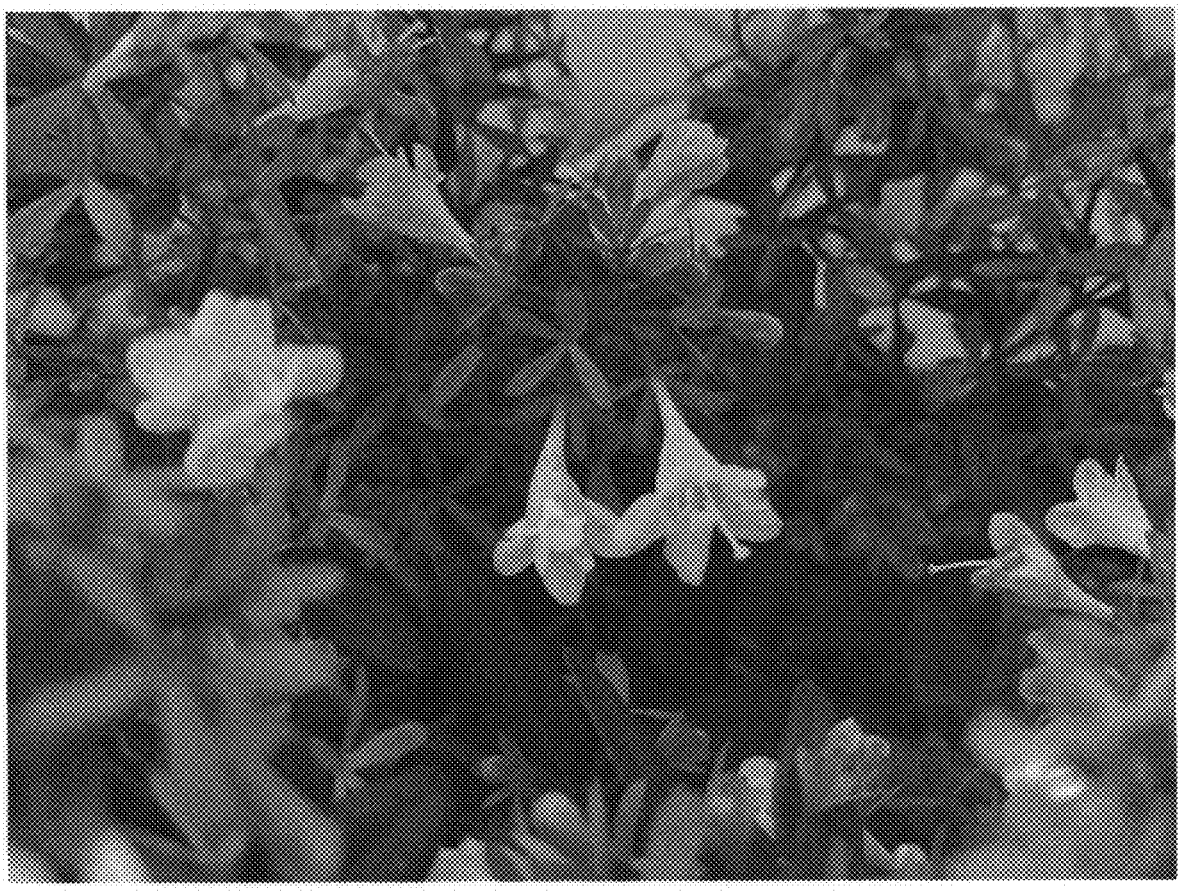

FIG. 2—illustrates a specimen of an inflorescence and sepals in the course of opening.

DETAILED BOTANICAL DESCRIPTION

The chart used in the identification of the colors is that of The Royal Horticultural Society (R.H.S. Colour Chart), 2015 edition, London, England. The terminology which precedes reference to the chart has been added to indicate the corresponding color in more common terms. The color values were determined in September 2020 under natural light conditions in Cochranville, Pa. The description is based on the observation of plants produced from cuttings from stock plants and grown in one-gallon containers for approximately five months in an outdoor nursery in Cochranville, Pa. Plants were pinched once after transplant.

Parentage:

*Female parent*.—Unnamed breeder seedling (non-patented).

*Male parent*.—Unknown.

Propagation:

*Type cutting*.—Terminal stem.

*Time to initiate roots*.—Approximately 10 to 14 days on average.

*Time to produce a rooted cutting*.—Approximately 21 to 25 days on average.

*Root description*.—Fibrous.

*Rooting habit*.—Freely branching.

Plant:

*Habit*.—Moderate growth vigor and compact, mounded and well-branched growth habit.

*Commercial crop time*.—Approximately 13 weeks from a rooted cutting to finish in a one-gallon container.

*Size*.—Approximately 30.0 cm in height from soil level to top of plant plane on average; and approximately 27.0 cm in width on average.

Branches:

*Branching habit*.—Freely branching, pinching enhances basal branching.

*Quantity of main branches per plant*.—Approximately 3 on average.

*Strength*.—Commonly strong, somewhat flexible and becomes woody with age.

*Size*.—Length: approximately 30.0 cm on average. Diameter: approximately 3.0 mm on average. Length of central internode: approximately 1.5 cm on average.

*Texture*.—Viscid, densely glandular pubescent.

*Color*.—Young stems: commonly near Greyed-Orange Group 173A. Mature stems: commonly near Brown Group 200C.

Foliage:

*Number of leaves*.—Approximately 14 per unbranched lateral stem on average; and approximately 196 per branched lateral stem on average.

*Form*.—Simple.

*Arrangement*.—Opposite.

*Durability to stress*.—Moderate to high.

Leaves:

*Shape*.—General: ovate. Margin: partially serrate. Apex: acute. Base: rounded.

*Venation pattern*.—Pinnate.

*Size*.—Length of mature leaf: approximately 2.4 cm on average. Width of mature leaf: approximately 1.0 cm on average.

*Texture*.—Upper and lower surfaces: smooth, glabrous, glossy.

*Color*.—Upper surface of mature foliage: commonly near Green Group NN137A with indistinguishable venation. Lower surface of mature foliage: commonly near Green Group 137C with venation commonly near Green Group 137.

*Petiole*.—Shape: rounded, slightly curved. Length: approximately 2.0 mm on average. Width: approximately 1.0 mm on average. Color: commonly near Green Group 137B.

Inflorescence:

*Quantity*.—Approximately 2 inflorescences per lateral stem, and approximately 30 flowers and buds per inflorescence on average.

*Type*.—Terminal compound cymes, self-cleaning with a persistent calyx.

*Fragrance*.—Moderately strong.

*Depth or height*.—Approximately 13.0 cm on average.

*Width*.—Approximately 9.0 cm on average.

*Rate of flower opening*.—Approximately 2 at a time per lateral branch.

Flower:

*Type*.—Single, campanulate.

*Aspect*.—Outward to slightly drooping.

*Bud*.—Shape: obovate. Length: approximately 1.3 cm on average. Diameter: approximately 4.0 mm on average. Color: commonly a blend of near Red-Purple Group 68B and Red-Purple Group 68C with near Yellow-White Group 158C at the apex. Rate of opening: approximately 3 days.

*Petals*.—Quantity: commonly 5, fused into an irregular campanulate shape. Appearance: slightly glossy. Shape: narrow oblong. Margin: entire. Apex: obtuse. Length: approximately 1.7 cm on average. Width of upper two petals: approximately 4.0 mm on average. Width of three lower petals: approximately 5.0 mm on average. Texture of upper and lower surfaces: smooth. Color of upper surface when first and fully open: commonly near Red-Purple Group 65D with a blend of near Red-Purple Group 65A. Color of lower surface when first and fully open: commonly near White Group N155C.

*Calyx*.—Shape: rotate. Length: approximately 5.0 mm on average. Diameter: approximately 1.0 cm on average.

*Sepals*.—Quantity per flower: commonly 5 on average. Length: approximately 5.0 mm on average. Width: approximately 2.0 mm on average. Shape: oblanceolate. Apex: acute. Base: cuneate. Margin: entire. Arrangement: rotate. Appearance: matte. Texture of upper and lower surfaces: smooth. Color of immature sepals: upper surface commonly near Greyed-Red Group 179C transitioning to near Yellow-Green Group 145C toward the base; lower surface commonly near Greyed-Red Group 180D transitioning to Yellow-Green Group 145D towards the base. Color of mature sepals: upper surface commonly near Greyed-Red Group 181B; lower surfaces commonly near Greyed-Red Group 181C.

*Pedicles*.—Strength: strong. Aspect: erect with secondary pedicels at an average angle of 40 degree. Length: approximately 3.0 mm on average. Width: approximately 0.5 mm on average. Texture: smooth, glabrous. Color: commonly near Yellow-Green Group 144B.

*Reproductive organs*.—Androecium: Stamen: commonly 4 per flower. Anther: shape is narrow oblong, versatile; length is approximately 2.0 mm on average; and coloration is commonly near Yellow-White Group 158C. Filament: length is approximately 1.3 cm on average and coloration is commonly near White Group 155B. Pollen: amount is moderate and coloration is commonly near Yellow-White Group 158C. Gynoecium: Pistil: commonly 1 per flower and length is approximately 1.8 cm on average. Stigma: shape is club and coloration is commonly near Yellow-White Group 158C. Style: length is approximately 1.7 cm on average and coloration is commonly near White Group 155B. Ovary: coloration is commonly near Yellow-Green Group 145C. Seed and fruit: none have been observed to date.

Development:

*Blooming*.—Freely flowering under outdoor growing conditions with substantially continuous blooming from summer through autumn.

*Lastingness of individual flower*.—Approximately 5 days on average.

*Tolerance to disease*.—Not observed to date.

The new 'Abesrpras' variety has not been observed under all possible environmental conditions to date. Accordingly, it is possible that the phenotypic expression may vary somewhat with changes in light intensity and duration, cultural practices, and other environmental conditions.

We claim:

1. A new and distinct cultivar of *Abelia* plant characterized by the following combination of characteristics:

(a) forms light-pink colored flowers with dark pink colored sepals, (b) displays medium green colored foliage, and (c) exhibits a moderately vigorous and compact and mounded growth habit;

substantially as herein shown and described.

* * * * *